US010898421B2

(12) United States Patent
Kerr et al.

(10) Patent No.: US 10,898,421 B2
(45) Date of Patent: Jan. 26, 2021

(54) ANTI-DANDRUFF COMPOSITION COMPRISING PYCNIDIONE AND EPOLONE

(71) Applicant: Croda International PLC, Yorkshire (GB)

(72) Inventors: Russell Greig Kerr, Charlottetown (CA); David Patrick Overy, Carleton Place (CA); Fabrice Berrué, Halifax (CA)

(73) Assignee: Croda International Plc

( * ) Notice: Subject to any disclaimer, the term of this patent is extended or adjusted under 35 U.S.C. 154(b) by 0 days.

(21) Appl. No.: 15/580,018

(22) PCT Filed: Jun. 8, 2016

(86) PCT No.: PCT/GB2016/051679
§ 371 (c)(1),
(2) Date: Dec. 6, 2017

(87) PCT Pub. No.: WO2016/198848
PCT Pub. Date: Dec. 15, 2016

(65) Prior Publication Data
US 2018/0168979 A1  Jun. 21, 2018

(30) Foreign Application Priority Data

Jun. 8, 2015  (GB) .................................. 1509847.8

(51) Int. Cl.
*A61K 8/35* (2006.01)
*A61K 8/49* (2006.01)
*A61Q 5/00* (2006.01)
*A61K 31/352* (2006.01)
*A61K 31/60* (2006.01)
*A61K 31/194* (2006.01)
*A61K 31/496* (2006.01)
*A61K 31/4412* (2006.01)
*A61Q 5/02* (2006.01)
*A61Q 5/12* (2006.01)
*C12P 17/06* (2006.01)
*C12P 17/18* (2006.01)

(52) U.S. Cl.
CPC ............... *A61K 8/498* (2013.01); *A61K 8/35* (2013.01); *A61K 31/194* (2013.01); *A61K 31/352* (2013.01); *A61K 31/4412* (2013.01); *A61K 31/496* (2013.01); *A61K 31/60* (2013.01); *A61Q 5/006* (2013.01); *A61Q 5/02* (2013.01); *A61Q 5/12* (2013.01); *C12P 17/06* (2013.01); *C12P 17/181* (2013.01)

(58) Field of Classification Search
CPC .......... A61K 8/498; A61K 8/35; A61Q 5/006
See application file for complete search history.

(56) References Cited

U.S. PATENT DOCUMENTS 5,284,866 A * 2/1994 Mayerl ................. C12P 17/181
514/453
2010/0184853 A1 7/2010 Hernandez et al.

FOREIGN PATENT DOCUMENTS

| DE | 19860543 A1 | 6/2000 | |
| EP | 1354586 A1 | 10/2003 | |
| WO | WO-9729733 A1 * | 8/1997 | ............... A61K 8/41 |
| WO | 2007096654 A2 | 8/2007 | |
| WO | 2008152127 A1 | 12/2008 | |
| WO | 2010061185 A2 | 6/2010 | |

OTHER PUBLICATIONS

Reeder et al, Antimicrobial Agents and Chemotherapy (2011), vol. 55(12), pp. 5753-5760. (Year: 2011).*
Printout of http://www.essentialchemicalindustry.org/materials-and-applications/surfactants.html, Mar. 18, 2013. (Year: 2013).*
Hunter et al, Journal of Surfactants and Detergents, vol. 1, No. 2 (Apr. 1998). (Year: 1998).*
Overy et al., "Sea Foam as a Source of Fungal Inoculum for the Isolation of Biologically Active Natural Products", Mycology: International Journal on Fungal Biology, vol. 5, No. 3, Sep. 19, 2014, pp. 130-144. (Year: 2014).*
Hsiao et al., "Pycnidione, a Fungus-derived Agent, Induces Cell Cycle Arrest and Apoptosis in A549 Human Lung Cancer Cells", Chemico-Biological Interactions vol. 197, 2012 pp. 23-30.
International Search Report and Written Opinion for International Application No. PCT/GB2016/051679, dated Aug. 1, 2016, 10 pages.
Ishikawa et al., "Pseurotin A and its Analogues as Inhibitors of Immunoglobuline E Production", Bioorganic & Medicinal Chemistry Letters, vol. 19, 2009, pp. 1457-1460.
Kang et al., "Culture Condition-dependent Metabolite Profiling of Aspergillus Fumigatus with Antifungal Activity", Fungal Biology, vol. 117, 2013, pp. 211-219.
Mo et al., "Naturally Occurring Tetramic Acid Products: Isolation, Structure Eludication and Biological Activity", RSC Advances., vol. 4, 2014, pp. 50566-50596.
Overy et al., "Sea Foam as a Source of Fungal Inoculum for the Isolation of Biologically Active Natural Products", Mycology:International Journal on Fungal Biology, vol. 5, No. 3, Sep. 19, 2014, pp. 130-144.
Wanner et al., "Epolones Induced Erythropoietin Expression via Hypoxia-inducible Factor-1 α Activation", Blood, vol. 96, No. 4, Aug. 15, 2000, pp. 1158-1565.

* cited by examiner

Primary Examiner — Craig D Ricci
Assistant Examiner — Janet L. Coppins
(74) Attorney, Agent, or Firm — RatnerPrestia

(57) ABSTRACT

Use of pycnidione, epolone A, and epolone B as anti-dandruff actives either alone or in combination in anti-dandruff compositions, particularly shampoos and conditioners. The actives are particularly effective against *Malassezia* yeasts and *Malassezia furfur*. A method of obtaining pycnidione, epolone A, and epolone B from culturing of *Neosetophoma samarorum* is also described.

21 Claims, No Drawings

ANTI-DANDRUFF COMPOSITION COMPRISING PYCNIDIONE AND EPOLONE

CROSS REFERENCE TO RELATED APPLICATIONS

This application is the National Stage filing of International Appln. No. PCT/GB2016/051679, filed Jun. 8, 2016, and claims priority of GB Application No. 1509847.8, filed Jun. 8, 2015, the entirety of which applications is incorporated herein by reference for all purposes.

The invention relates generally to the use of *Neosetophoma samarorum* (*N. samarorum*) to produce biologically active compounds including pycnidione, epolone A, and epolone B, and the use of these compounds each or in combination as anti-dandruff agents.

Anti-dandruff compositions, particularly shampoos, are well known and have been commercially available for many years. Many anti-dandruff actives have been used commercially such as ketoconazole, zinc pyrithione, piroctone olamine, octopirox, salicylic acid, selenium sulphide, coal tar, and azelaic acid. These actives generally function as anti-microbial/fungal agents, being effective against certain species and strains of fungi and/or bacteria. For example, the yeast-like fungus *Malassezia* lives on the scalp of most adults, but for some people it irritates the scalp and can cause more skin cells to grow. Although *Malassezia* yeasts are a part of the normal microflora, under certain conditions they can cause superficial skin infection. These extra skin cells die and fall off, making them appear white and flaky in hair and on clothes. Thus, materials which are active against *Malassezia*, in particular the species *Malassezia furfur*, can reduce the severity of dandruff.

These topic antifungal preparations are often combined with a cortisonic drug to control the inflammation and alleviate the pain and itching. However, the use of these molecules may not produce satisfactory results, and in some cases these compounds exhibit an intrinsic and undesired cytotoxicity.

Based on these findings, there is a need for compounds which demonstrate anti-fungal activity against *Malassezia* yeasts. There is a continual requirement for improved anti-dandruff actives and end-use products containing such actives. There is a need for anti-dandruff actives that have improved, including broad spectrum, activity against fungi and/or bacteria, or that function other than by antimicrobial effects; that do not have the environmental concerns of some existing actives, and/or in use are non-irritant to the skin.

There is also a need for an anti-dandruff effect to be obtained from the use of a wide range of hair care products such as a shampoo, conditioner, 2-in-1 shampoo/conditioner, leave-on hair tonic, spray, liquid rinse, gel or mousse etc. Ideally, an anti-dandruff active should be capable of being effective in a wide range of hair care products.

The present invention also seeks to provide compounds in a hair care formulation, where the compound may provide comparable or improved anti-dandruff properties compared to existing anti-dandruff agents.

The present invention also seeks to provide the use of compounds as anti-dandruff agents, and formulations comprising said compounds for use in reducing dandruff on human skin.

According to a first aspect of the present invention there is provided an anti-dandruff composition comprising an effective amount of at least one of pycnidione, epolone A, or epolone B, or any combination thereof.

According to a second aspect of the present invention there is provided a method of forming an anti-dandruff composition which comprises mixing together:
  (i) at least one of pycnidione, epolone A, or epolone B, or any combination thereof;
  (ii) at least one surfactant; and
  (iii) water.

According to a third aspect of the present invention there is provided the use of at least one of pycnidione, epolone A, and/or epolone, or in any combination thereof, as active ingredient in an anti-dandruff composition.

According to a fourth aspect of the present invention there is provided an anti-dandruff shampoo or conditioner comprising:
  at least one of pycnidione, epolone A, and/or epolone, or any combination thereof;
  a surfactant; and
  optionally one or more of a betaine, a non-ionic surfactant, an amphoteric surfactant, and a cationic surfactant.

According to a fifth aspect of the present invention there is provided a method of providing anti-dandruff efficacy which comprises the steps of:
  (i) wetting the hair with water;
  (ii) applying an effective amount of an anti-dandruff composition comprising at least one of pycnidione, epolone A, or epolone B, or any combination thereof, to the hair;
  (iii) rinsing the anti-dandruff composition from the hair using water; and
  (iv) optionally repeating steps (ii) and (iii).

According to a sixth aspect of the present invention there is provided a method for killing or retarding the growth of *Malassezia* spp., the method comprising the step of contacting the *Malassezia* spp. with a composition comprising at least one of pycnidione, epolone A, and/or epolone, or any combination thereof, effective to kill or retard the growth of *Malassezia* spp.

According to a seventh aspect of the present invention there is provided a method of obtaining pycnidione, epolone A, or epolone B comprising the steps of:
  culturing *Neosetophoma samarorum* in a medium under conditions which promote the metabolic synthesis of a molecule selected from the group consisting of: pycnidione, epolone A, or epolone B from the *Neosetophoma samarorum*; and
  purifying the synthesised molecule from the cultured medium.

We have surprisingly discovered that the compounds pycnidione, epolone A, and epolone B, each provide for an anti-dandruff composition that overcomes and/or significantly reduces at least one of the aforementioned problems.

It has been found that pycnidione, epolone A, and epolone B provide for compounds having good anti-dandruff properties, and which also have good cytotoxicity, formulability, and are active at lower pH.

As used herein, the terms 'for example,' for 'instance,' 'such as,' or 'including' are meant to introduce examples that further clarify more general subject matter. Unless otherwise specified, these examples are provided only as an aid for understanding the applications illustrated in the present disclosure, and are not meant to be limiting in any fashion.

The term 'anti-dandruff composition' refers to the provision of effects for preventing and/or treating scalp dandruff. This includes preventing and/or reducing excessive dandruff formation, and/or visually unappealing excessively formed dandruff.

The pycnidione, epolone A, and epolone B will be understood to be anti-dandruff actives, and will collectively be referred to as such throughout. Any such references will be understood to include a reference to each active alone, or any combination of two or more of said actives.

It will be understood that pycnidione refers to a bistropolone compound having a structure of formula (I);

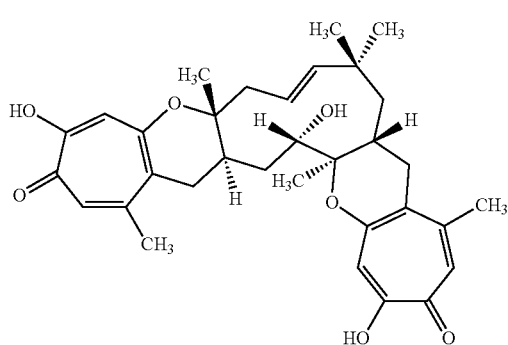

(I)

Additionally, reference to pycnidione will include dehydroxypycnidione (in which the hydroxyl group on the ten membered ring is a hydrogen), and eupenifeldin (pycnidione stereoisomer). Pycnidione is preferred.

It will be understood that epolone A refers to the sesquiterpene-tropolone compound having a structure of formula (II);

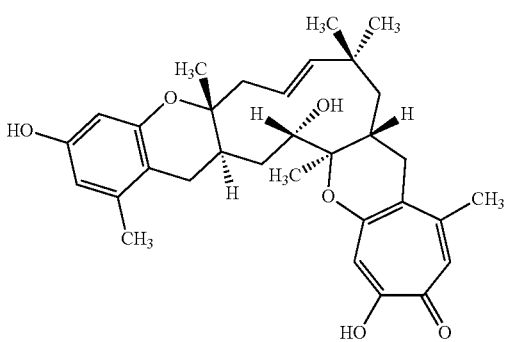

(II)

It will be understood that epolone B refers to the tropolone compound having a structure of formula (III);

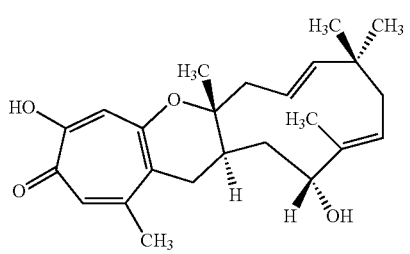

(III)

All three of the compounds, pycnidione, epolone A, and epolone B will be understood to individually provide anti-dandruff activity.

The pycnidione, epolone A, and epolone B can each be formed and extracted from cultures of *Neosetophoma samarorum* (*N. samarorum*), and specifically isolate RKDO834. The extract can be purified to isolate desired compounds from the culture medium.

The desired compounds can be extracted and purified from the culture liquid or the fungal biomass by any means ordinarily used for generally collecting microbial metabolites. Examples include chromatography with adsorbent such as various ion exchange resins, nonionic adsorbing resins, gel filtration chromatography, activated charcoal, alumina and silica gel, or a separation method by using high performance liquid chromatography, or crystallization, concentration under reduced pressure, or lyophilisation. Any of said means can be used alone, in appropriate combination thereof, or repeatedly.

The cultures of *N. samarorum*, can be obtained from natural sources or from culture collections such as Centraalbureau voor Schimmelcultures (Utrecht, Netherlands). Isolates of *N. samarorum* can be cultured by methods known in the art of mycology.

As a means of producing the compounds of the present invention, the producing organism can be grown on any suitable synthetic mediums or natural medium so long as they appropriately contain carbon sources, nitrogen sources, and inorganic salts. If necessary, mediums may be suitably supplemented with vitamins and other nutrient substances. Examples of general carbon sources include (but are not limited to), sugars such as glucose, maltose, fructose, sucrose, and starch, alcohols such as glycerol, and mannitol, amino acids such as glycine, alanine, and asparagine, and oils and fats such as soy bean oil and olive oil. Examples of the nitrogen source include organic nitrogen-containing compounds such as soy bean powder, corn steep liquor, beef extract, peptone, yeast extract, amino acid mixtures, and fish powder, and inorganic nitrogen compounds such as ammonium salts and nitrates. As well micro-nutrients in the form of inorganic salts can be used, for example, calcium carbonate, sodium chloride, potassium chloride, magnesium sulphate, copper sulphate, manganese chloride, zinc sulphate, cobalt chloride, and various phosphates.

The organism can be grown in an appropriate cultivation temperature within a range that allows growth of a microorganism and effective production of the compounds of the present invention. Preferred cultivation temperature is from 10° C. to 32° C., and more preferably from 20° C. to 25° C. pH at the beginning of the cultivation is preferably from about 6 to 8, and cultivation period of time is in the range of one day to a few weeks.

The cultivation may be terminated when a produced amount of the compound of the present invention reaches to an amount suitable for collection, preferably reaches the maximum amount. As a cultivation method, any method can be suitably employed such as solid layer cultivation and normal stirring cultivation.

For example, isolates of *N. samarorum* can be plated onto nutrient-containing (e.g., YM (Yeast extract Malt extract) and OA (oatmeal)) agar, and incubated for several days at room temperature until observable colonies appear. Individual *N. samarorum* colonies on the agar can be assayed for production of pycnidione, epolone A, and/or epolone B.

Those colonies producing the desired molecules can be used to inoculate a broth culture (e.g., a YM broth culture), which can be cultured under suitable conditions (e.g., at room temperature with shaking for several days) to yield a seed inoculum. The seed inoculum can be used to initiate larger liquid cultures (e.g., in a rice-based growth medium such as 10 g brown rice and 25 mL of YNB (Yeast Nitrogen Base) broth which can be incubated for several days (e.g., 4-28 days) at about room temperature to expand the *N. samarorum* culture.

The culture can then be mixed and a suitable solvent [e.g., 1:1 (v:v) EtOAc:MeOH solution] can be added. After shaking, the culture medium-solvent mixture can be filtered, and the filtered solvent extract (containing pycnidione, epolone A, and/or epolone B) dried prior to further chemical purification. Chemical purification can be performed by any suitable method, e.g., fractionation using a C18 column followed by reverse phase HPLC to obtain purified pycnidione, epolone A, or epolone B. Fractions containing the purified product can be determined by any suitable method such as NMR. This process could be performed by any chromatography means.

In other embodiments, pycnidione, epolone A, and epolone B might be obtained from other available resources (typically other fungi). For example, pycnidione may be isolated from the fermented broth of Theissenia rogersii 92031201, and pycnidione, epolone A, and epolone B can be isolated from OS-F69284 (ATCC 74390). Pycnidione, epolone A, and epolone B might also be made by synthetic techniques.

Derivatives and analogues of the purified pycnidione, epolone A, and epolone B can be made using methods generally known in the art of organic and medicinal chemistry. These derivatives and analogues can be assayed for anti-fungal activity and toxicity by the methods described herein. Those that exhibit high anti-fungal activity and low toxicity can be selected for use.

The anti-dandruff activity of the compounds described herein can be analysed by adapting methods well known in the art.

One aspect of the invention includes a method for killing or retarding the growth of a multicellular or unicellular fungus, by contacting the microorganism with pycnidione, epolone A, and/or epolone B. The ability and amount of pycnidione, epolone A, and/or epolone B to kill or retard the growth of a particular microorganism can be determined by the methods described herein.

Toxicity of compositions including pycnidione, epolone A, and/or epolone B can be assessed using conventional cell- or animal-based assays. For example, as described below, keratinocyte and fibroblast cell lines can be used in an assay to determine the concentration of pycnidione, epolone A, and/or epolone B that is cytotoxic to such cells. Likewise other in vitro cellular cytotoxicity or mutagenicity assays can be used. Animal-based assays for analysing the toxicity of a compound might include acute toxicity, subchronic toxicity, chronic toxicity, carcinogenicity, reproductive toxicity, dermal toxicity, ocular toxicity, neurotoxicity, and genetic toxicity assays.

A particular feature of the actives of the present invention is the combination of low cytotoxicity, good anti-dandruff activity, and stability and retention of activity even at lower pH values.

In particular, the MIC cytotoxicity of the actives against keratinocyte cells according to the method described in the examples is preferably greater than 5 μg per ml, more preferably greater than 10 μg per ml, further preferably greater than 20 μg per ml, most preferably greater than 40 μg per ml.

The $IC_{50}$ cytotoxicity of the actives against keratinocyte cells according to the method described in the examples is preferably greater than 2 μg per ml, more preferably greater than 5 μg per ml, further preferably greater than 8 μg per ml, most preferably greater than 10 μg per ml.

The MIC cytotoxicity of the actives against fibroblast cells according to the method described in the examples is preferably greater than 5 μg per ml, more preferably greater than 10 μg per ml, further preferably greater than 20 μg per ml, most preferably greater than 40 μg per ml.

The $IC_{50}$ cytotoxicity of the actives against fibroblast cells according to the method described in the examples is preferably greater than 2 μg per ml, more preferably greater than 5 μg per ml, further preferably greater than 8 μg per ml, most preferably greater than 10 μg per ml.

With regard to activity against anti-dandruff, the MIC cytotoxicity of the actives against *M. furfur* cells according to the method described in the examples is preferably less than 130 μg per ml, more preferably less than 100 μg per ml, further preferably less than 80 μg per ml, most preferably less than 30 μg per ml. In particular, less than 12 μg per ml.

The $IC_{50}$ cytotoxicity of the actives against *M. furfur* cells according to the method described in the examples is preferably less than 100 μg per ml, more preferably less than 60 μg per ml, further preferably less than 30 μg per ml, most preferably less than 20 μg per ml. In particular, less than 10 μg per ml.

As a measure of the anti-dandruff activity in relation to the cytotoxicity to skin cells (keratinocyte and fibroblast) a value of MIC (*M. furfur*) divided by MIC (keratinocyte/fibroblast) can be defined, with lower values desired. A value of 1 would therefore represent equal anti-dandruff and cytotoxicity, whereas a value below 1 would represent higher anti-dandruff activity with lower cytotoxicity. The actives of the present invention may have a value less than 3. Preferably, less than 1. Further preferably, less than 0.5. More preferably, less than 0.3. Most preferably, less than 0.2.

The same parameter may also be calculated with reference to $IC_{50}$ values rather than MIC. The actives of the present invention may have a value less than 5. Preferably, less than 2. Further preferably, less than 1. More preferably, less than 0.8. Most preferably, less than 0.6.

The actives described herein, derivatives and analogues thereof, and suitable salts of the foregoing can be included along with one or more excipients to make anti-dandruff compositions which can be administered by a variety of routes, including topical, and especially dermal.

The actives described herein, derivatives and analogues thereof, and suitable salts of the foregoing can be included as active ingredients in non-pharmaceutical anti-dandruff compositions (i.e., those that usually do not require a prescription from a physician or other health care provider). Non-pharmaceutical compositions can include those that are formulated into shampoos, other hair care products (e.g. conditioners, styling products, etc.), soaps, lotions or ointments, medicated wipes, anti-fungal sprays, and the like.

The compositions can be in the form of elixirs, suspensions, emulsions, solutions, syrups, aerosols (as a solid or in a liquid medium), ointments, or lotions. Liquid forms of the compositions include aqueous solutions, aqueous or oil suspensions, and emulsions.

The anti-dandruff composition is preferably a hair care product such as a shampoo, conditioner, 2-in-1 shampoo/conditioner, hairspray, hair spritz, hair colouring product, leave-on hair tonic, hair sunscreen product, styling mousse or gel, or other hair treatment composition.

As used herein, 'effective amount' includes within its meaning a non or low toxic but sufficient amount of the anti-dandruff actives to provide the desired effect (i.e.

improvement in dandruff). In particular, the amount would be sufficient to be effective to kill or retard the growth of *Malassezia furfur*, but low enough to avoid serious side effects (e.g. undue toxicity or allergic reaction).

The anti-dandruff composition according to the present invention suitably comprises in the range from 0.001 wt. % to 20 wt. %, preferably 0.01 wt. % to 10 wt. %, more preferably 0.1 wt. % to 5 wt. %, particularly 0.2 wt. % to 2 wt. %, and especially 0.3 wt. % to 1.2 wt. % of the anti-dandruff actives, based on the total weight of the composition. Most preferably, 1.0 wt. % or less.

The pycnidione, epolone A, and/or epolone B defined herein may be the only anti-dandruff actives present in the anti-dandruff composition, i.e. the anti-dandruff composition comprises only anti-dandruff actives that consist essentially of, or consist of, the pycnidione, epolone A, and/or epolone B. Each of pycnidione, epolone A, and/or epolone B may be used alone or in any combination with one or more of the other three.

In an alternative embodiment, the pycnidione, epolone A, and/or epolone B may be used in combination with at least one other (i.e. chemically different) anti-dandruff active material such as anti-fungal drugs elected from any of the following: nystatin, cuprimyxin, tolnaftate, candicidin, haloprogin, iodochlorohydroxyquin, clotrimazole, undecylenic acid, proprionic acid, caprylic acid, benzoic acid, salicylic acid, griseofulvin, amphotericin B, ketoconazole, miconazole, filipin, hamycin, natamycin, rimocidin, bifonazole, butoconazole, econazole, fenticonazole, isoconazole, omoconazole, oxiconazole, sertaconazole, sulconazole, tioconazole, albaconazole, fluconazole, isavuconazole, itraconazole, posaconazole, ravuconazole, terconazole, voriconazole, abafungin, amorolfin, butenafine, naftifine, terbinafine, anidulafungin, caspofungin, micafungin, ciclopirox olamine, flucytosine, crystal violet, piroctone olamine, zinc pyrithione, selenium sulphide, tar, and tea tree oil.

If present, preferably the other anti-dandruff actives may be selected from the group consisting of ketoconazole, zinc pyrithione (ZPT), piroctone olamine, octopirox, salicylic acid, selenium sulphide, coal tar, azelaic acid, climbazole, salicylic acid, undecylenic acid, and mixtures thereof.

One preferred other anti-dandruff active is pyrithione and/or a metal salt thereof. Any form of metal, preferably polyvalent, pyrithione salts may be used, including those in platelet and needle form. Preferred salts include those formed from the polyvalent metals magnesium, barium, bismuth, strontium, copper, zinc, cadmium, zirconium, and mixtures thereof. Zinc is preferred, particularly the zinc salt of 1-hydroxy-2-pyridinethione (known as zinc pyrithione (ZPT)).

If present, the anti-dandruff composition according to the present invention suitably comprises in the range from 0.01 wt. % to 15 wt. %, preferably 0.1 wt. % to 5 wt. %, more preferably 0.2 wt. % to 2 wt. %, particularly 0.3 wt. % to 1 wt. %, and especially 0.4 wt. % to 0.6 wt. % of at least one other anti-dandruff active (i.e. other than the anti-dandruff actives defined herein), based on the total weight of the composition.

In one embodiment, the ratio by weight of anti-dandruff actives to pyrithione and/or a metal salt thereof, preferably ZPT, present in the anti-dandruff composition is suitably 0.1 to 10:1, preferably 0.33 to 3:1, more preferably 0.5 to 2:1, particularly 0.8 to 1.2:1, and especially 0.9 to 1.1:1.

The anti-dandruff composition may also comprise a zinc-containing layered mineral, for example zinc carbonate (basic), hydrozincite (zinc carbonate hydroxide), aurichalcite (zinc copper carbonate hydroxide), and rosasite (copper zinc carbonate hydroxide).

If present, the anti-dandruff composition comprises in the range from 0.01 wt. % to 10 wt. %, preferably 0.2 wt. % to 5 wt. %, more preferably 0.4 wt. % to 2 wt. %, particularly 0.5 wt. % to 1 wt. %, and especially 0.6 wt. % to 0.8 wt. % of a zinc-containing layered mineral, preferably zinc carbonate, based on the total weight of the composition.

The anti-dandruff composition comprises at least one surfactant. The surfactant may be selected from anionic, non-ionic, amphoteric and/or cationic surfactants. Preferably, the surfactant may be anionic surfactant.

Suitable anionic surfactants include alkyl sulphates, alkyl ether sulphates, alpha olefin sulphonates, sulphosuccinates, isethionates, acyl amides, acyl glutamates, alkyl ether carboxylates and alkyl phosphates. The alkyl group preferably comprises in the range from 6 to 30, more preferably 8 to 20, particularly 10 to 14, and especially 12 carbon atoms. Alkyl ether sulphates and/or alkyl sulphates are preferred, particularly alkali metal, e.g. sodium, and/or ammonium salts thereof. Lauryl ether sulphate and/or lauryl sulphate are particularly preferred anionic surfactants.

In one embodiment, the anti-dandruff composition comprises both alkyl ether sulphate and alkyl sulphate, preferably lauryl ether sulphate and lauryl sulphate, suitably present at a weight ratio of 1 to 15:1, preferably 3 to 10:1, more preferably 4 to 8:1, particularly 5 to 7:1, and especially 5.5 to 6.5:1.

Surfactants can be included in an amount ranging from 0.1 wt. % to 50 wt. % by weight, preferably from 5 wt. % to 30 wt. %, more preferably from 10 wt. % to 25 wt. % by weight of the total shampoo composition.

The concentration of surfactant, preferably anionic surfactant, in the anti-dandruff composition is suitably in the range from 0.5 wt. % to 25 wt. %, preferably 3 wt. % to 20 wt. %, more preferably 7 wt. % to 18 wt. %, particularly 10 wt. % to 16 wt. %, and especially 12 wt. % to 14 wt. % based on the total weight of the composition.

The anti-dandruff composition may also contain at least one secondary surfactant. If present, the secondary surfactant may be selected from a non-ionic, amphoteric, betaine, and/or cationic surfactant. The total concentration of surfactant and secondary surfactant(s) in the composition may suitably be in the range from 3 wt. % to 50 wt. %, preferably 8 wt. % to 40 wt. %, more preferably 12 wt. % to 30 wt. %, particularly 16 wt. % to 25 wt. %, and especially 18 wt. % to 22 wt. % based on the total weight of the composition.

Suitable betaines include alkyl betaines, alkylamido betaines, alkyl sultaines, alkylamido sultaines, and mixtures thereof. Alkylamido betaines are preferred. The alkyl group preferably comprises in the range from 6 to 30, more preferably 8 to 20, and particularly 10 to 14 carbon atoms. If present, the concentration of betaine surfactant in the anti-dandruff composition may preferably be in the range from 0.1 wt. % to 20 wt. %, more preferably 0.5 wt. % to 10 wt. %, particularly 1 wt. % to 12 wt. %, and especially 1.5 wt. % to 2.5 wt. % based on the total weight of the composition.

Suitable non-ionic surfactants include the fatty alcohol acid or amide ethoxylates, alkanolamides and alkoxylated alkanolamides, monoglyceride ethoxylates, sorbitan ester ethoxylates, alkyl polyglycosides, ethylene glycol monoesters, ethylene glycol diesters, and mixtures thereof. If present, the concentration of non-ionic surfactant in the anti-dandruff composition may preferably be in the range from 0.1 wt. % to 30 wt. %, more preferably 0.5 wt. % to 10 wt. %, particularly 1 wt. % to 5 wt. %, and especially 1.5 wt. % to 2 wt. % based on the total weight of the composition.

Suitable amphoteric surfactants include alkylimino-diproprionates, alkylamphoglycinates, alkylamphoprionates, alkylamphoacetates (mono- and di-), N-alkyl beta-aminoproprionic acids, alkylpolyamino carboxylates, phosphorylated imidazolines, and mixtures thereof. If present, the concentration of amphoteric surfactant in the anti-dandruff composition may preferably be in the range from 0.1 wt. % to 20 wt. %, more preferably 0.5 wt. % to 10 wt. %, particularly 1 wt. % to 5 wt. %, and especially 1.5 wt. % to 2 wt. % based on the total weight of the composition.

Suitable cationic surfactants include alkyl quaternaries, benzyl quaternaries, ester quaternaries, ethoxylated quaternaries, alkyl amines, and mixtures thereof. The alkyl group preferably comprises in the range from 6 to 30, more preferably 8 to 22, and particularly 10 to 20 carbon atoms.

The cationic surfactant may also be a polyquaternium material (or polyquat). Polyquats include polymers based on acrylamide and/or dimethyl allylamonium chloride such as Polyquaternium 6, Polyquaternium 7, and the like. Polymeric quaternium ammonium salts of guar gum, such as guar hydroxypropyltrimonium chloride, may be used. Polymeric quaternium ammonium salts of cellulose such as Polyquaternium 10 and the like, and polymeric quaternium ammonium salts of starch, may also be used.

If present, the concentration of cationic surfactant in the anti-dandruff composition may preferably be in the range from 0.1 wt. % to 20 wt. %, more preferably 0.1 wt. % to 10 wt. %, particularly 0.3 wt. % to 3 wt. %, and especially 0.5 wt. % to 1 wt. % by weight based on the total weight of the composition.

The anti-dandruff composition can also include other cosmetically acceptable ingredients, and in the case of hair care composition those which are suitable for topical application to the hair.

The anti-dandruff actives can be mixed with or diluted by an excipient in the anti-dandruff composition. When the excipient serves as a diluent, it can be a solid, semi-solid, or liquid material, which acts as a vehicle, carrier or medium for the active ingredient. Examples of suitable excipients include: lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose.

The anti-dandruff composition may additionally comprise: lubricating agents such as talc, magnesium stearate, and mineral oil; wetting agents; emulsifying and suspending agents; preserving agents such as methyl- and propylhydroxy-benzoates; sweetening agents; and flavouring agents.

The anti-dandruff composition may be formulated as transparent or opaque emulsions, lotions, creams, pastes or gels.

The anti-dandruff composition may comprise water. The amount of the water in the anti-dandruff composition may suitably be in the range from 10 wt. % to 97 wt. %, preferably 30 wt. % to 95 wt. %, more preferably 50 wt. % to 90 wt. %, particularly 65 wt. % to 85 wt. %, and especially 72 wt. % to 78 wt. %, based on the total weight of the composition.

The anti-dandruff composition of the present invention may be used with one or more of the other standard ingredients or carriers used in hair care products, including shine enhancers, moisturisers, herbal additives, hair strengtheners, vitamin additives, colorants, hair thickening agents; setting and styling agents; ultraviolet absorbers; silicone oils; essential oils and fragrances; thickening or viscosity-enhancing agents; detergents; stabilising agents; emollients; chelating agents; sequestering agents; preservatives; disinfectants; anti-oxidants/radical scavengers; antistatic agents; conditioning agents; detangling ingredients; emulsifying or dispersing agents; stimulants; soothers; solvents; carriers and the like.

In particular, the anti-dandruff composition may comprise a silicone fluid or oil such as dimethylpolysiloxane, dimethyl silicone, highly polymerised methyl polysiloxane, and methyl polysiloxane, known generically as dimethicone, cyclic oligomeric dialkylsiloxanes, such as the cyclic oligomers of dimethylsiloxane, known generically as cyclomethicone. The concentration of silicone oil in the anti-dandruff composition may preferably be in the range from 0.1 wt. % to 40 wt. %, more preferably 0.3 wt. % to 20 wt. %, particularly 0.5 wt. % to 5 wt. %, and especially 1 wt. % to 1.5 wt. % based on the total weight of the composition.

The anti-dandruff composition may be in the form of an aqueous "leave on" or an aqueous "rinse off" end-use product. For such compositions, a dilute solution of the anti-dandruff actives in water may be used. The concentration of the anti-dandruff actives in such a product is preferably in the range from 0.01 wt. % to 5 wt. %, more preferably 0.2 wt. % to 2 wt. %, particularly 0.5 wt. % to 1.5 wt. %, and especially 0.9 wt. % to 1.1 wt. % based on the total weight of the composition. Preferably, a buffered solution is used, in which the pH of the solution is adjusted to mildly acidic, with a pH in the range of from 4 to 6. In the case of rinse-off formulations, instructions are provided to wash off the diluted anti-dandruff actives composition after application. Depending on the level of treatment required, such instructions may also require the product to remain on the hair for some time, such as from 1 to 30 minutes. For leave-on formulations, the washing off step is omitted.

One preferred anti-dandruff product is a hair shampoo or conditioner, which functions to make the hair more shiny and manageable. The shampoo or conditioner may be in the form of a dispersion, emulsion or solution. One preferred system is one that forms liquid crystals. The liquid crystals are preferably lyotropic liquid crystals (i.e. both concentration and temperature dependent), more preferably lamellar phase liquid crystals, and particularly L alpha phase (neat) liquid crystals. The concentration of the anti-dandruff actives in the shampoo or conditioner is preferably in the range from 0.1 wt. % to 10 wt. %, more preferably 0.3 wt. % to 2 wt. %, particularly 0.4 wt. % to 1.5 wt. %, and especially 0.5% to 1 wt. % based on the total weight of the composition.

The shampoo or conditioner may contain many different types of functional ingredients such as;
(i) cationic hair conditioning agents, e.g. ethoxylated phosphate fatty quats, such as those sold by Croda as Arlasilk; fatty amido amines, such as those sold by Croda as Incromine™; fatty quats, such as those sold by Croda as Incroquat™ Crodazosoft™, Rejuvasoft™ or VibraRiche™ typically used at a concentration in the range from 1 wt. % to 5 wt. % based on the total weight of the composition. These are typically combined with polymeric hair conditioning cationic materials such as quaternised cellulose sold by Croda as Crodacel™, quaternised proteins, such as those sold by Croda, as Croquat™, Crolactin™, Crosilkquat™, Keramimic™ and Hydrotriticum™.
(ii) fatty alcohols, e.g. stearyl, cetearyl, cetyl, oleyl alcohols, used typically at a concentration range of 2 wt. % to 5 wt. % based on the total weight of the composition.

(iii) humectants or solvents, e.g. alcohols and polyols such as glycerol and polyethylene glycols, when used typically at a concentration in the range from 1 wt. % to 10 wt. % based on the total weight of the composition;

(iv) reconstructors, e.g. hydrolysed proteins such as wheat protein, which function to penetrate the hair and strengthen the hair structure through polymer cross-linking;

(v) glossing or detangling materials which bind to the hair and reflect light, e.g. silicones such as dimethicone, phenyltrimethicone, dimethiconol and/or trimethylsilylamodimethicone, usually at a concentration in the range from 0.2 wt. % to 10 wt. % based on the total weight of the composition;

(vi) acidity regulators, e.g. citric acid, lactic acid, which generally maintain the pH of the conditioner at about 4 to 6;

(vii) thermal protectors, usually heat-absorbing polymers, which shield the hair against excessive heat, e.g. caused by blow-drying or curling irons or hot rollers such as for instance those sold by Croda as Mirustyle™ MFP (quaternised starch); and (viii) UV protection agents, to protect hair or formulation components from degradation by UV light, such as those sold by Croda as Crodasorb™ UV-HPP.

In one embodiment, the anti-dandruff composition of the invention is in the form of an emulsion (or dispersion), such as an oil-in-water or water-in-oil emulsion, particularly an oil-in-water emulsion.

The oil phase of the emulsion will preferably be mainly an emollient oil of the type used in personal care or cosmetic products. The emollient can and usually will be an oily material which is preferably liquid at ambient temperature. Alternatively, it can be solid at ambient temperature, in which case in bulk it will usually be a waxy solid, provided it is liquid at an elevated temperature at which it can be included in and emulsified in the composition.

Suitable normally liquid emollient oils include non-polar oils, for example mineral or paraffin, especially isoparaffin, oils, such as that sold by Croda as Arlamol™ HD; or medium polarity oils, for example vegetable ester oils such as jojoba oil, vegetable glyceride oils, animal glyceride oils, such as that sold by Croda as Crodamol™ GTCC (caprylic/capric triglyceride), synthetic oils, for example synthetic ester oils, such as isopropyl palmitate and those sold by Croda as Estol™ 1512, ether oils, particularly of two fatty e.g. C8 to C18 alkyl residues, such as that sold by Cognis as Cetiol OE (dicaprylether), guerbet alcohols such as that sold by Cognis as Eutanol G (octyl dodecanol), or silicone oils, such as dimethicone oil such as those sold by Dow Corning as DC200, cyclomethicone oil, or silicones having polyoxyalkylene side chains to improve their hydrophilicity; or highly polar oils including alkoxylate emollients for example fatty alcohol propoxylates such as that sold by Croda as Arlamol™ E (propoxylated stearyl alcohol).

The concentration of the oil phase may vary widely. The amount of the oil phase in the emulsion is preferably in the range from 0.5 wt. % to 80 wt. %, more preferably 1 wt. % to 30 wt. %, particularly 1.5 wt. % to 15 wt. %, and especially 2 wt. % to 10 wt. %, based on the total weight of the emulsion.

The amount of the aqueous phase in the emulsion is preferably in the range from 20 wt. % to 99.5 wt. %, more preferably 70 wt. % to 99 wt. %, particularly 85 wt. % to 98.5 wt. %, and especially 90 wt. % to 98 wt. %, based on the total weight of the emulsion.

A wide range of emulsifiers may be employed, particularly one or more cationic emulsifier(s). The specific nature of the emulsifier surfactant used in any particular instance depends on the type of emulsion being made, particularly the amount and nature of the oil being emulsified and the total desired level of emulsifier.

The concentration of emulsifier in the emulsion is preferably in the range from 0.1 wt. % to 20 wt. %, more preferably 0.5 wt. % to 15 wt. %, particularly 1 wt. % to 10 wt. %, and especially 2 wt. % to 7 wt. %, based on the total weight of the emulsion.

The emulsion suitably comprises in the range from 0.01 wt. % to 10 wt. %, preferably 0.5 wt. % to 5 wt. %, more preferably 0.1 wt. % to 4 wt. %, particularly 0.2 wt. % to 2 wt. %, and especially 0.3 wt. % to 1 wt. % of the anti-dandruff composition based on the total weight of the emulsion.

Many other components that may be used in hair care compositions or end-use products may also be included in the anti-dandruff composition according to the present invention. These components may be oil soluble, water soluble or non-soluble. Examples of such materials include:

(i) preservatives such as those based on parabens (alkyl esters of 4-hydroxybenzoic acid), phenoxyethanol, substituted ureas and hydantoin derivatives, e.g. those sold commercially under the trade names Germaben II Nipaguard BPX and Nipaguard DMDMH, when used usually in a concentration in the range from 0.5 wt. % to 2 wt. % based on the total weight of the composition;

(ii) perfumes, when used typically at a concentration in the range from 0.1 wt. % to 10 wt. % more usually up to about 5 wt. % and particularly up to about 2 wt. %, based on the total weight of the composition;

(iii) humectants or solvents such as alcohols, polyols such as glycerol and polyethylene glycols, when used typically at a concentration in the range from 1 wt. % to 10 wt. % based on the total weight of the composition;

(iv) alpha hydroxy acids such as glycolic, citric, lactic, malic, tartaric acids and their esters; self-tanning agents such as dihydroxyacetone;

(v) vitamins and their precursors including: (a) Vitamin A, e.g. as retinyl palmitate and other tretinoin precursor molecules, (b) Vitamin B, e.g. as panthenol and its derivatives, (c) Vitamin C, e.g. as ascorbic acid and its derivatives, (d) Vitamin E, e.g. as tocopheryl acetate, (e) Vitamin F, e.g. as polyunsaturated fatty acid esters such as gamma-linolenic acid esters;

(vi) skin care agents such as ceramides either as natural materials or functional mimics of natural ceramides;

(vii) natural phospholipids, e.g. lecithin;

(viii) vesicle-containing formulations;

(ix) botanical extracts with beneficial skin care properties;

(x) skin whiteners such as kojic acid, arbutin and similar materials;

(xi) skin repair compounds actives such as Allantoin and similar series;

(xii) caffeine and similar compounds;

(xiii) cooling additives such as menthol or camphor;

(xiv) insect repellents such as N,N-diethyl-3-methylbenzamide (DEET) and citrus or *eucalyptus* oils;

(xv) essential oils; and (xvi) pigments, including microfine pigments, particularly oxides and silicates, e.g. iron oxide, particularly coated iron oxides, and/or titanium dioxide, and ceramic materials such as boron nitride, or other solid components, such as are used in make-up and cosmetics, to give suspoemulsions, typically used in an amount in the range from 1 wt. % to 15 wt. %, but usually at least 5 wt. %, and particularly about 10 wt. % based on the total weight of the composition.

Application of the anti-dandruff composition, particularly a shampoo, to the hair typically includes working the composition through the hair. One preferred method for providing anti-dandruff efficacy comprises the steps of;
(i) wetting the hair with water;
(ii) applying an effective amount of the anti-dandruff composition to the hair; and
(iii) rinsing the anti-dandruff composition from the hair using water.

These steps may be repeated, in order to obtain the desired cleansing, conditioning, and anti-dandruff effect sought.

An alternative method comprises the steps of;
(i) wetting the hair with water;
(ii) applying an effective amount of the anti-dandruff shampoo composition;
(iii) rinsing the shampoo composition from the hair using water;
(iv) applying an effective amount of a conditioner composition optionally containing the anti-dandruff actives defined herein;
(v) rinsing the conditioner composition from the hair using water.

A preferred embodiment of the method is when both the shampoo composition and the conditioner composition comprise the anti-dandruff actives.

All of the features described herein may be combined with any of the above aspects, in any combination.

In order that the present invention may be more readily understood, reference will now be made, by way of example, to the following description.

It will be understood that all tests and physical properties listed have been determined at atmospheric pressure and room temperature (i.e. 25° C.), unless otherwise stated herein, or unless otherwise stated in the referenced test methods and procedures.

EXAMPLE 1—FORMING & EXTRACTION OF ANTI-DANDRUFF ACTIVES

Bioassay-guided fractionation of culture extracts led to the isolation of three biologically active metabolites produced by the fungus *N. samarorum*. The isolate RKDO834 along with reference strains of *N. samarorum* including the type strain were obtained from the Centraalbureau voor Schimmelcultures (Utrecht, Netherlands), plated out on YM (Yeast extract Malt extract) and OA (oatmeal) agar, and incubated for 14 days at 22° C. Colony morphology was observed and eight explants (approximately 10 mm³) were aseptically removed into glass scintillation vials, to which 15 mL of EtOAc was added and the vials were shaken for 1 hr at 200 rpm. The resulting EtOAc extract was then removed from the vial and dried down under a stream of air and retained for chemical analysis.

Additionally eight colony explants (approximately 3 mm³) were aseptically removed into 15 mL of YM broth in a sterile, capped 50 ml test tube containing 2 sterile glass coverslips and shaken at 200 rpm, 22° C. for 5 days to create a seed inoculum. A 500 μL aliquot of seed inoculum was removed into a sterile 2 mL Eppendorf tube, centrifuged at 10000 rpm for 5 minutes to pellet the mycelia and allow for the removal of the broth by pipetting, and stored frozen at −20° C. prior to DNA extraction. The seed inoculum was also streak plated onto YM and LB (Lysogeny Broth) agar (25 g LB Broth MILLER, 18 g agar in 1 L diH2O) plates, incubated for 3 days at 22° C. and inspected to ensure inoculum purity.

An additional 500 μL of seed inoculum from strain RKDO834 was dispensed into a capped 250 mL Erlenmyer flask containing an autoclave sterilised rice-base growth medium (10 g brown rice and 25 mL of YNB broth (6.7 g YNB powder, 5 g sucrose, 18 g instant ocean, 1 L diH2O)) and incubated at 22° C. for 21 days. After the incubation period, colony growth upon the rice-based medium was disturbed using a spatula and 40 mL of a 1:1 (v:v) EtOAc: MeOH solution was added and the capped flask was shaken for 60 minutes at 175 rpm. The contents of the flask were then filtered through Whatman #3 filter paper using a glass vacuum chamber with a Buchner funnel and the filtered solvent extract was dried down under a stream of air prior to further chemical purification.

The extract obtained from the rice-based culture of RKDO834 was fractionated into 4 fractions on a Thermo HyperSep C18 column (500 mg C-18, 6 ml column volume) using a vacuum manifold by eluting with 14 mL of 4 different solvent combinations: 8:2 diH$_2$O:MeOH (fraction 1), 1:1 diH$_2$O:MeOH (fraction 2), EtOH (fraction 3), and 1:1 MeOH:DCM (fraction 4). The eluent representing fractions 2-4 were retained and dried down under air, weighed and submitted for antimicrobial testing against a pathogen panel. Fraction 3 was further fractionated on a Thermo HyperSep Diol column (500 mg Diol, 6 ml column volume) using a vacuum manifold by eluting with 14 mL of three different solvent combinations: 9:1 hexane:tBME (diol fraction 1), 9:1 tBME:MeOH (diol fraction 2), MeOH (diol fraction 3). Each fraction was retained, dried down under air and submitted for bioassay.

Preparative HPLC fractionation of diol fraction 2 was performed on a reverse phase HPLC column (Gemini 5μ, C18 column, 10×250 mm) using a Thermo electron HPLC coupled with UV and evaporative light scattering detector (ELSD). Initial fractionation of diol fraction 2 was carried out with isocratic elution of 85% aqueous MeCN with a flow rate 2.5 mL/min yielding eight sub fractions. Bioactivity was determined for each of the sub-fractions and followed up by an additional fractionation step. Fractionation of sub-fraction 2 with isocratic elution of 85% aqueous MeCN (2.5 mL/min) yielded pure epolone B. Both sub-fraction 3 and sub-fraction 4 were further fractionated using isocratic conditions of 70% aqueous MeCN (2.5 mL/min) to yield pure pycnidione and epolone A respectively.

NMR spectra were recorded on a Bruker Avance III 600 MHz NMR spectrometer operating at 600 and 150 MHz for $^1$H and $^{13}$C, respectively. Spectra were referenced to residual undeuterated solvent peaks. Optical rotation was measured on a Rudolp Autopol III polarimeter. Analytical mass spectrometry of all samples was carried out on a Thermo Scientific Accela UHPLC coupled with a Thermo Exactive electrospray mass spectrometer (ESI-MS), with a SEDEX 80LT ELSD and a Thermo photodiode array (PDA) detector. Chromatography was carried out on a Kinetex 1.7μ C18, 2.1×50 mm column using a gradient of 95:5% diH$_2$O:MeCN with 0.1% formic acid-100% MeCN with 0.1% formic acid in 4 min, held at 100% MeCN with 0.1% formic acid for 5 min and returned to 95:5% diH$_2$O:MeCN with 0.1% formic acid-100% MeCN with 0.1% formic acid and held at these conditions for 1 min.

Antifungal activity of the initial HyperSep C-18 fractions of the crude culture extract generated from the fermentation of RKDO834 on rice medium was observed from fraction 3. Fraction 3 was selected for further bioassay-guided fractionation by HPLC to ultimately afford three separate metabolites demonstrating anti-*Malassezia* activity. Purification of the first compound yielded 0.44 mg and mass spectrometrical analysis confirmed a protonated molecular ion ([M+H]$^+$) of 385.2375 m/z ([M+MeCN+H]$^+$425.2498 m/z also observed). NMR data and an optical rotation of [α]$_D$ ([α]$_D^{27.8}$+81.1 (0.05, CH$_2$Cl$_2$) matched with literature data confirming the metabolite as epolone B (Cal et al., 1998).

Purification of the second bioactive metabolite yielded 3.47 mg of a compound having a [M+H]$^+$ ion of 549.2853 m/z ([M+MeCN+H]$^+$589.2973 m/z also observed) and NMR signals matched reported literature values confirming the identity of the compound as pycnidione. An optical rotation [α]$_D$ ([α]$_D^{27.8}$+260.7 (0.3, CH$_2$Cl$_2$) confirmed the stereochemistry of the molecule. Purification of the third metabolite yielded 0.64 mg of a compound having a [M+H]$^+$ of 521.2898 m/z ([M+MeCN+H]$^+$561.3018 m/z). NMR and specific optical rotation data Gab ([α]$_D^{27.8}$+210.2 (0.07, CH$_2$Cl$_2$)) matched with literature values for epolone A.

Ethyl acetate culture extracts generated for RKDO834 and each of the representative *N. samarorum* strains were analysed and compared for secondary metabolite production. All strains produced the compounds epolones A and B and pycnidione as confirmed by mass spectral and UV data. All four strains differed in the relative quantities of epolone A and B produced compared to pycnidione, as inferred from ELSD data. In all of the culture extracts examined, pycnidione was one of the more predominant metabolites observed after 14 days growth on solid YM media.

Anti-Fungal Activity Examples

The terms Minimum Inhibitory Concentration and Half Maximal Inhibitory Concentration will be understood to have the following meanings.

Minimum Inhibitory Concentration (MIC)

The minimum inhibitory concentration (MIC) will be understood to represent the lowest concentration of an antimicrobial that will inhibit the visible growth of a microorganism after overnight incubation.

Half Maximal Inhibitory Concentration (IC$_{50}$)

The half maximal inhibitory concentration (IC$_{50}$) is a measure of the effectiveness of a substance in inhibiting a spec biological or biochemical function. This quantitative measure indicates how much of a particular drug or other substance (inhibitor) is needed to inhibit a given biological process (or component of a process, i.e. an enzyme, cell, cell receptor or microorganism) by half. IC$_{50}$ represents the concentration of an active that is required for 50% inhibition in-vitro.

EXAMPLE 2 PYCNIDIONE ANTI-FUNGAL ACTIVITY

*Malassezia furfur* (ATCC #38593) was cultured on Media C agar for 7 days at 37° C. Yeast colonies were then harvested into 0.9% saline sterile diH2O and diluted to approximately 1.5×106 CFU/mL using a 0.5 MacFarland standard (Fisher #R20410) to create an assay inoculum. Assay inoculum was added to sterile Media C broth to a final concentration of 4.5×104 CFU/mL. Assays were carried out in 96 well plates with a final well volume of 100 µL.

Extract fractions and pure compounds were tested in triplicate against each organism. Extract fractions and pure compounds were re-suspended in sterile 20% DMSO. Extract fractions were assayed at two concentrations (50 and 250 µg/mL) with a final well volume concentration of 2% DMSO, while pure compounds were serially diluted to generate a range of eight concentrations (128 µg/mL to 1 µg/mL) in a final well volume concentration of 2% DMSO.

Each plate contained eight un-inoculated positive controls (media+20% DMSO), eight untreated negative controls (Media+20% DMSO+organism), and one column containing a concentration range of a ketoconazole as a control antibiotic. The assay plate was incubated at 37° C. for 5 days after which growth within the wells were visualised and photographed with a UVP Biospectrum 500 imaging system. Alamar blue was then added to each well at 10% of the culture volume (11 µL in 100 µL). Fluorescence was monitored using a BioTek Synergy HT plate reader at 530/25 excitation, 590/35 emission and 35 sensitivity at both time zero and 4 hours after Alamar blue was added. After subtracting the time zero emission 590 nm measurement from the final reading the inferred percentage of microorganism survival relative to vehicle control wells were calculated and the IC50 was determined.

Human foreskin BJ fibroblast cells (ATCC CRL-2522) were grown and maintained in 15 mL of Eagle's minimal essential medium (Sigma M5650) supplemented with 10% fetal bovine serum (VWR #CA95043-976) and 100 µU penicillin and 0.1 mg/mL streptomycin (VWR #CA12001-692) in T75 cm2 cell culture flasks (VWR #CABD353136) at 37° C. in a humidified atmosphere of 5% CO$_2$. Culture medium was refreshed every two to three days and cells were not allowed to exceed 80% confluency.

Adult human epidermal keratinocytes (Heka) isolated from skin (Invitrogen #C-005-5C) were grown and maintained in 15 mL of EPilife medium (Invitrogen #M-EPI-500) supplemented with HKGS growth supplements (Invitrogen #S-001-5) (0.2% v/v bovine pituitary extract (BPE), 5 µg/mL bovine insulin, 0.18 µg/mL hydrocortisone, 5 µg/mL bovine transferrin, 0.2 ng/mL human epidermal growth factor) and 50 µg/mL gentamicin (Sigma #G1397-10ML) in T75 cm2 cell culture flasks (VWR #CABD353136) and incubated at 37° C. in a humidified atmosphere of 5% CO$_2$. Growth medium was refreshed every 2 days until the cells reached 50% confluency and then the medium was refreshed every 24 hours until 80% confluency was obtained.

At 80% confluency, the cells were counted, diluted and plated into 96 well treated cell culture plates (VWR #29442-054) at a cell density of 10000 cells per well in 90 µL of respective growth medium. All media used for the assay were the same without the addition of antibiotics. The plates were incubated at 37° C. in a humidified atmosphere of 5% CO$_2$ to allow cells to adhere to the plates for 24 hrs before treatment. DMSO was used as the vehicle at a final concentration of 1% in the wells.

All compounds to be tested were resolubilised in sterile DMSO (Sigma #D2438) and a dilution series was prepared for each cell line using the respective cell culture growth medium of which 10 µL were added to the respective assay plate well yielding eight final concentrations ranging from 128 µg/mL to 1 µg/mL per well (final well volume of 100 µL) and incubated at 37° C. in a humidified atmosphere of 5% CO$_2$ for 24 hrs.

All samples were tested in triplicate. Each plate contained eight un-inoculated positive controls (media+20% DMSO), eight untreated negative controls (Media+20% DMSO+cells). Alamar blue (Invitrogen #Dal1100) was added, 24 hrs after treatment, to each well at 10% of the culture volume (11 µL in 100 µL). Fluorescence was monitored using a BioTek Synergy HT plate reader at 530/25 excitation, 590/35 emission and 35 sensitivity at both time zero and 4 hrs after Alamar blue was added. After subtracting the time zero emission 590 nm measurement from the final reading the inferred percentage of microorganism survival relative to vehicle control wells were calculated and the $IC_{50}$ was determined.

The results of the anti-dandruff actives of the invention are shown in Table 1. Keratinocyte and fibroblast are both skin cells representing various layers of the epidermis, so clearly cytotoxicity against these cells should be within acceptable limits.

TABLE 1

Anti-dandruff active comparison (all values in µg/mL)

| Active Used | M. furfur | | Keratinocyte | | Fibroblast | |
|---|---|---|---|---|---|---|
| | MIC | $IC_{50}$ | MIC | $IC_{50}$ | MIC | $IC_{50}$ |
| Pycnidione | 8 | 6 | 64 | 15 | 64 | 11 |
| Epolone A | 64 | 48 | 32 | 13 | 32 | 14 |
| Epolone B | 32 | 24 | >128 | 50 | >128 | >128 |

Antifungal activity against the dandruff causing fungus *M. furfur* as observed for each of the compounds tested, most notably pycnidione which showed an MIC of 8 µg/ml (IC50 of 6 µg/ml).

The compounds pycnidione, epolone A, and epolone B were found to have varying degrees of cytotoxicity against both the keratinocyte and the fibroblast cell lines. Regarding pycnidione, no cell line cytotoxicity was observed at lower concentrations where inhibition of *Malassezia* yeasts is still retained (ie. 8 µg/ml). Therefore a therapeutic window exists for the safe use of pycnidione in the treatment of *Malassezia* yeasts.

Pycnidione (MIC 64 µg/ml; $IC_{50}$ 15 m/ml) is has very low toxicity to keratinocyte cells compared to existing active zinc pyrithione (MIC 1 µg/ml; IC50 0.75 µg/ml), the most commonly used active ingredient found in anti-dandruff shampoo formulations.

When formulating pycnidione in an off-the-shelf shampoo composition (J&J baby shampoo) it was found that the composition remained stable after a two month period.

It is to be understood that the invention is not to be limited to the details of the above embodiments, which are described by way of example only. Many variations are possible.

The invention claimed is:

1. An anti-dandruff composition comprising 0.001 wt. % to 20 wt. % of at least one of pycnidione, epolone A, or epolone B, or any combination thereof, based on the total weight of the composition.

2. The anti-dandruff composition according to claim 1, which has a MIC cytotoxicity against *M. furfur* cells of less than 130 µg per ml.

3. The anti-dandruff composition according to claim 1, which has an IC50 cytotoxicity against *M. furfur* cells of less than 100 µg per ml.

4. The anti-dandruff composition according to claim 1, wherein the pycnidione, epolone A, and/or epolone B are the only anti-dandruff actives present in said composition.

5. The anti-dandruff composition according to claim 1, wherein said composition comprises at least one other anti-dandruff active material.

6. The anti-dandruff composition according to claim 5, wherein said other anti-dandruff active material is selected from the group consisting of ketoconazole, zinc pyrithione (ZPT), piroctone olamine, octopirox, salicylic acid, selenium sulphide, coal tar, azelaic acid, climbazole, undecylenic acid, and mixtures thereof.

7. The anti-dandruff composition according to claim 5, which comprises 0.01 wt. % to 15 wt. % of said other anti-dandruff active material.

8. The anti-dandruff composition according to claim 5, wherein said other anti-dandruff active material is zinc pyrithione (ZPT).

9. The anti-dandruff composition according to claim 1, which comprises 0.01 wt. % to 10 wt. % of least one of pycnidione, epolone A, or epolone B, or any combination thereof, based on the total weight of the composition.

10. The anti-dandruff composition according to claim 1, which comprises 0.001 wt. % to 10 wt. % of least one of pycnidione, epolone A, or epolone B, or any combination thereof, based on the total weight of the composition.

11. The anti-dandruff composition according to claim 1, which comprises 0.001 wt. % to 5 wt. % of least one of pycnidione, epolone A, or epolone B, or any combination thereof, based on the total weight of the composition.

12. The anti-dandruff composition according to claim 1, which contains pycnidione.

13. The anti-dandruff composition according to claim 1, which contains pycnidione and does not contain epolone A or epolone B.

14. The anti-dandruff composition according to claim 1, which is in the form of a member selected from the group consisting of shampoos, conditioners, hair styling products, soaps, lotions, ointments, medicated wipes, anti-fungal sprays, elixirs, suspensions, emulsions, solutions, syrups, aerosols, aqueous solutions, aqueous or oil suspensions, emulsions, hair coloring products, leave-on hair tonics, hair sunscreen products, creams, pastes and gels.

15. The anti-dandruff composition according to claim 1, which further comprises at least one surfactant.

16. The anti-dandruff composition according to claim 15, wherein said surfactant is a non-ionic surfactant, an amphoteric surfactant, or a cationic surfactant.

17. The anti-dandruff composition according to claim 15, which comprises 0.1 wt. % to 50 wt. % of said surfactant.

18. The anti-dandruff composition according to claim 15, which further comprises at least one betaine.

19. The anti-dandruff composition according to claim 1, wherein the pycnidione, epolone A, or epolone B are obtained from *Neosetophoma samarorum*.

20. A method of treating dandruff in hair, comprising applying an effective amount of the composition according to claim 1 to the hair.

21. A method of preparing the composition according to claim 16, comprising combining at least one of pycnidione, epolone A, or epolone B, or any combination thereof, and said surfactant.

\* \* \* \* \*

UNITED STATES PATENT AND TRADEMARK OFFICE
CERTIFICATE OF CORRECTION

PATENT NO. : 10,898,421 B2
APPLICATION NO. : 15/580018
DATED : January 26, 2021
INVENTOR(S) : Russell Greig Kerr, David Patrick Overy and Fabrice Berrué

Page 1 of 1

It is certified that error appears in the above-identified patent and that said Letters Patent is hereby corrected as shown below:

On the Title Page

Item (73) Assignee: "Croda International Pie" should read --Croda International Plc--

Signed and Sealed this
Eleventh Day of May, 2021

Drew Hirshfeld
*Performing the Functions and Duties of the
Under Secretary of Commerce for Intellectual Property and
Director of the United States Patent and Trademark Office*